(12) United States Patent
Preston-Powers

(10) Patent No.: US 9,737,103 B2
(45) Date of Patent: Aug. 22, 2017

(54) BRAIN COOLING DEVICE

(71) Applicant: Jullian Joshua Preston-Powers, Hove (GB)

(72) Inventor: Jullian Joshua Preston-Powers, Hove (GB)

(*) Notice: Subject to any disclaimer, the term of this patent is extended or adjusted under 35 U.S.C. 154(b) by 643 days.

(21) Appl. No.: 14/160,506

(22) Filed: Jan. 21, 2014

(65) Prior Publication Data

US 2014/0130239 A1 May 15, 2014

Related U.S. Application Data

(62) Division of application No. 12/865,326, filed as application No. PCT/GB2009/000273 on Jan. 30, 2009, now abandoned.

(30) Foreign Application Priority Data

Feb. 1, 2008 (GB) .................................. 0801908.5

(51) Int. Cl.
| | |
|---|---|
| A42B 3/04 | (2006.01) |
| A42B 3/12 | (2006.01) |
| A42B 3/00 | (2006.01) |
| A61F 7/00 | (2006.01) |
| A42B 3/28 | (2006.01) |
| A61F 7/10 | (2006.01) |
| A61F 7/02 | (2006.01) |

(52) U.S. Cl.
CPC .............. *A42B 3/0406* (2013.01); *A42B 3/00* (2013.01); *A42B 3/12* (2013.01); *A42B 3/285* (2013.01); *A61F 7/106* (2013.01); *A61F 2007/0002* (2013.01); *A61F 2007/0276* (2013.01)

(58) Field of Classification Search
CPC ....... A42B 3/0486; A42B 3/04; A42B 3/0406; A42B 3/06; A42B 3/10; A42B 3/121; A42B 3/122; A42B 3/12; A42B 3/285; A42B 1/008; A42B 1/08; A42B 3/063; A42B 3/064; A42B 3/00; A61F 2007/0002; A61F 2007/0008; A61F 2007/0007; A61F 7/02; A61F 7/106; A61F 2007/0293; A61F 2007/0093; A61F 2007/0233; A61F 2007/0276; A41D 13/0053; A41D 13/018
USPC ...... 2/7, 8.1, 411, 413, 425, 8; 607/109, 110, 607/114
See application file for complete search history.

(56) References Cited

U.S. PATENT DOCUMENTS

| | | | | |
|---|---|---|---|---|
| 4,133,055 A | * | 1/1979 | Zebuhr | A42B 3/121 2/411 |
| 4,172,495 A | * | 10/1979 | Zebuhr | A42B 3/285 165/46 |
| 4,382,446 A | * | 5/1983 | Truelock | A61F 7/03 607/110 |
| 4,551,858 A | * | 11/1985 | Pasternack | A42B 3/285 2/171.2 |

(Continued)

*Primary Examiner* — Amy Vanatta
(74) *Attorney, Agent, or Firm* — Edwin D. Schindler

(57) ABSTRACT

A headwear device includes an endothermic reactor and a trigger to initiate an endothermic reaction in a reactor while the headwear device is being worn on a wearer's head. The headwear device may preferably be utilized in, or conjunction with, a motorcycle safety helmet or similar crash protection device. The headwear device is intended to prevent or delay the onset of brain damage as a result of serious trauma or head injury.

16 Claims, 15 Drawing Sheets

(56) References Cited

U.S. PATENT DOCUMENTS

| | | | | |
|---|---|---|---|---|
| 4,580,547 | A * | 4/1986 | Kapralis | A61F 7/03 126/263.03 |
| 4,784,678 | A * | 11/1988 | Rudick | F25D 5/02 206/217 |
| 4,853,980 | A * | 8/1989 | Zarotti | A42B 3/285 2/413 |
| 4,920,963 | A * | 5/1990 | Brader | A61F 7/106 607/109 |
| 5,261,399 | A * | 11/1993 | Klatz | A61F 7/10 607/104 |
| 5,539,934 | A * | 7/1996 | Ponder | A42B 3/285 2/413 |
| 6,030,412 | A * | 2/2000 | Klatz | A61F 7/00 607/104 |
| 6,277,143 | B1 * | 8/2001 | Klatz | A61F 7/00 607/104 |
| 8,713,716 | B2 * | 5/2014 | Krueger | A41D 13/0002 2/412 |
| 2002/0068152 | A1 * | 6/2002 | Heath | A42B 3/10 428/178 |
| 2003/0055473 | A1 * | 3/2003 | Ramsden | A61F 7/10 607/109 |
| 2006/0005291 | A1 * | 1/2006 | Bedford | A42C 5/04 2/7 |
| 2006/0030916 | A1 * | 2/2006 | Lennox | A61F 7/0085 607/104 |
| 2006/0191277 | A1 * | 8/2006 | Defosset | A41D 13/0053 62/259.3 |
| 2007/0150033 | A1 * | 6/2007 | Johnson | A61F 7/106 607/114 |
| 2009/0276018 | A1 * | 11/2009 | Brader | A61F 7/10 607/104 |
| 2010/0137951 | A1 * | 6/2010 | Lennox | A61F 7/02 607/104 |
| 2011/0078845 | A1 * | 4/2011 | McKinney | A42B 3/285 2/422 |
| 2012/0151664 | A1 * | 6/2012 | Kirshon | A42B 3/12 2/413 |
| 2012/0210490 | A1 * | 8/2012 | Harty | A42B 3/285 2/171.2 |
| 2012/0233745 | A1 * | 9/2012 | Veazie | A42B 3/121 2/413 |
| 2013/0211484 | A1 * | 8/2013 | Rozental | A42B 3/122 607/110 |
| 2013/0298316 | A1 * | 11/2013 | Jacob | A42B 3/12 2/414 |
| 2015/0313305 | A1 * | 11/2015 | Daetwyler | A42B 3/121 2/414 |
| 2016/0100794 | A1 * | 4/2016 | Miller | A61B 5/4836 607/110 |
| 2016/0219965 | A1 * | 8/2016 | Sansone | A42B 3/285 |

* cited by examiner

Fig. 12
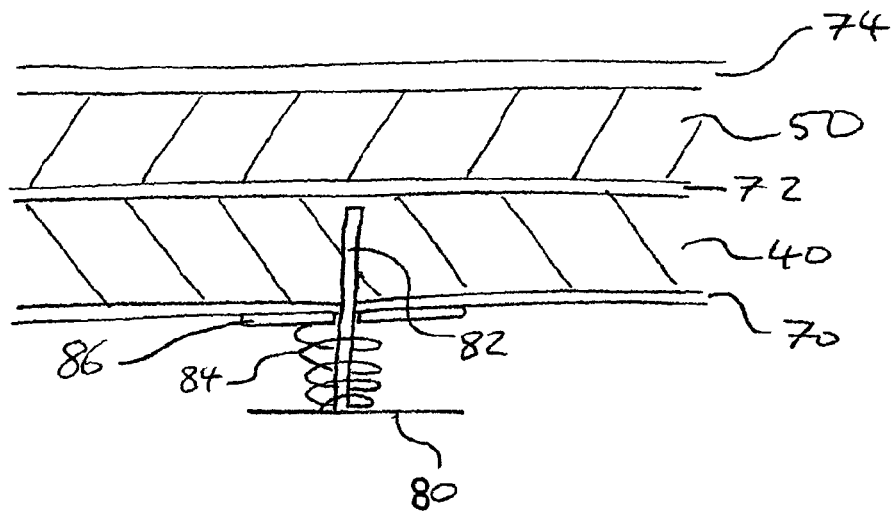
(A)
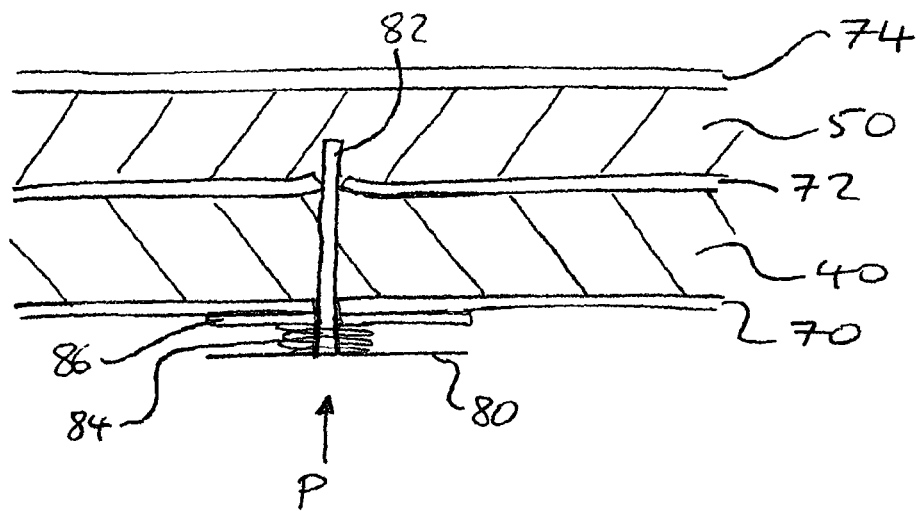
(B)
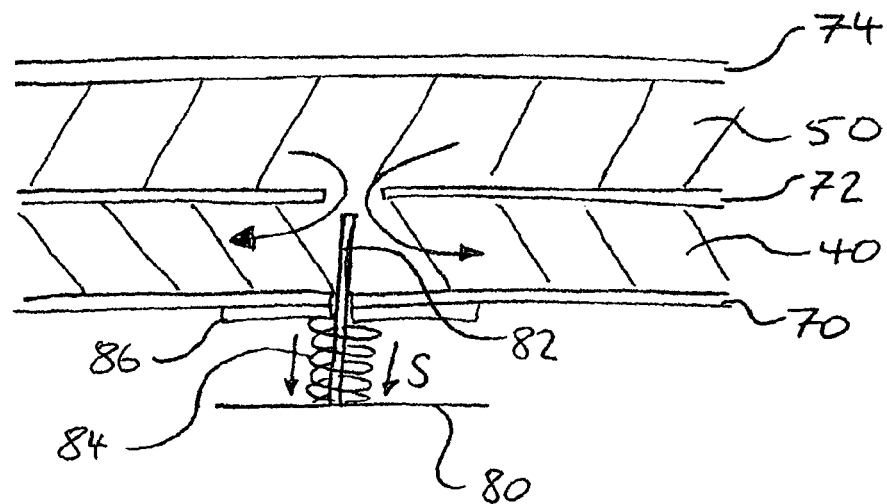
(C)

Fig. 13
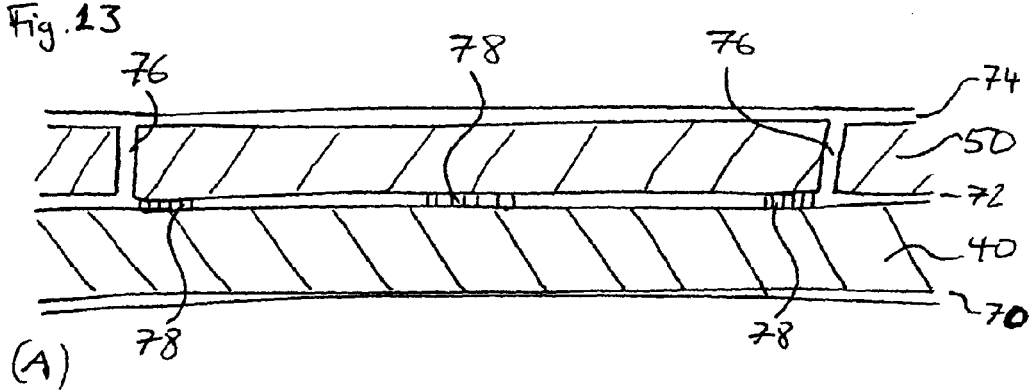
(A)
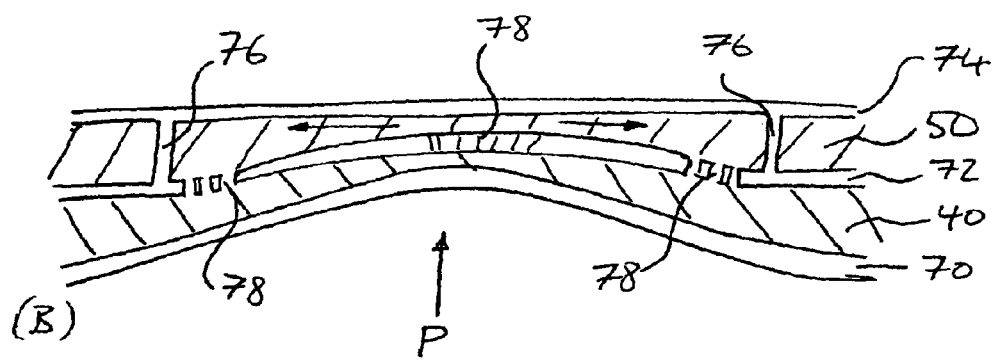
(B)
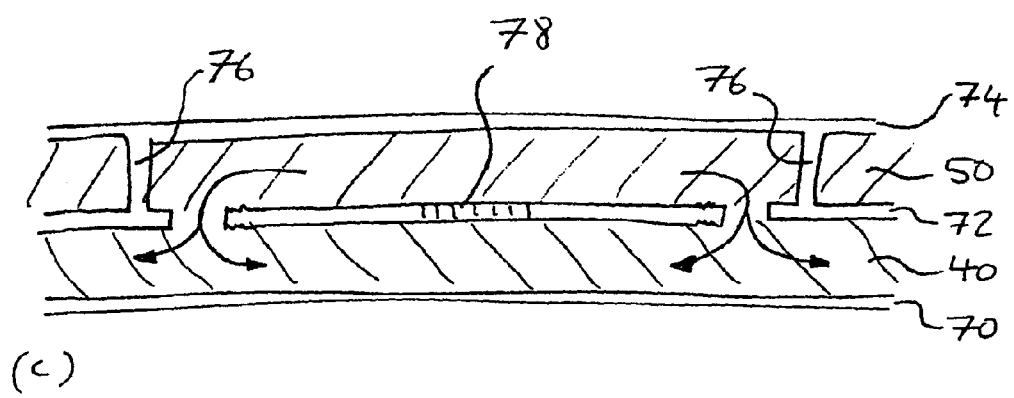
(C)

BRAIN COOLING DEVICE

CROSS-REFERENCE TO PRIOR APPLICATIONS

This is a division of U.S. patent application Ser. No. 12/865,326, now abandoned, which represented the United States National Phase patent application of P.C.T. International Application No. PCT/GB2009/000273, filed Jan. 30, 2009.

TECHNICAL FIELD

The present invention relates to headwear comprising an endothermic reactor. Such headwear is particularly suited to use as or in conjunction with safety headwear, such as motorcycle helmets.

BACKGROUND

It has long been recognised that neurological deterioration in trauma victims is dramatically reduced when a hypothermic state is induced. This phenomenon has been observed, for example, when an accident victim has fallen into cold, icy water resulting in hypothermia. A similar phenomenon was observed during the Napoleonic Wars, when wounded soldiers who were left "out in the cold" managed to survive their injuries, whilst their counterparts who had been warmed by a nearby fire perished. More recently, medical practitioners have made use of this phenomenon by deliberately inducing mild hypothermia in patients, prior to emergency treatment or during surgical operations. This causes the body's vital functions to be slowed down, thus reducing the chances of brain damage occurring in the patient. In extreme circumstances, the patient's core temperature can be reduced by submerging the patient in a bath of ice water, or by pumping cold fluids through or next to their internal organs. Cooling has also been noted to be particularly effective when applied directly to the patient's head.

The human skull has many small holes passing through it, known as emissary foramina, through which veins transport (hot) blood from the scalp into the venous sinuses. The blood transported to the surface of the head is cooled by the surrounding environment and by sweat evaporating from the surface of the skin, before re-entering the skull at a lower temperature, to help keep the brain cool. This explains how cooling the head at the surface can produce significant cooling within the human brain, even at significant depths within the skull, more quickly than would be expected to be achieved through mere thermal conduction.

Cranial cooling has been noted to reduce brain damage and increase survival rates in accident victims, and patients with head injuries are often treated in accident and emergency departments by cooling the patient's head. It is, however, often the case that a victim will have suffered their injuries significantly in advance of their arrival at a hospital "Accident and Emergency" department. If the delay between receiving an injury and receiving treatment at a hospital or other medical care facility is too long, significant neurological deterioration may already have occurred in the interim, and brain damage may thereafter be unavoidable. The sooner that effective brain cooling can be applied to victims of serious injury, the more effective the cooling will be to prevent the onset of brain damage. The crews of emergency response vehicles are often the first on site with any means for treating a victim of severe injuries, but as yet paramedic teams do not widely carry head-cooling apparatus as part of their standard equipment, if at all. What is required is an easily portable means of equipment by which paramedics and other emergency medical practitioners can easily and effectively apply head cooling to victims of serious injury in danger of suffering neurological deterioration as a result of their injuries sustained. One proposed solution is a nasal spray device, which administers a fine mist of PFCs (perfluorochemicals) into a patient's nasal cavity. The mist droplets evaporate on contact with the back of the nose to absorb heat and carry it away from the nose, which in turn cools the brain.

One particular group of injured patients liable to have sustained head injuries are motorcycle accident victims. Due to the exposed and unrestrained position of a motorcycle rider on their vehicle, motorcyclists who are involved in accidents often sustain severe injuries. By far the most common cause of fatalities amongst motorcycle accident victims, however, are head injuries resulting in brain trauma. Since as far back as 1946, it has been recognised that wearing a motorcycle safety helmet significantly reduces the chances of a motorcycle crash victim suffering a fatal injury. It is now recommended, if not a requirement of law, in almost all developed countries, to wear a motorcycle safety helmet when riding a motorcycle, and various safety standards have been set out which define the minimum performance requirements that a safety helmet must achieve in order to qualify for sale under the appropriate standards in the relevant territories.

A typical motorcycle safety helmet design is shown in FIGS. 1 to 3 of the present application. FIG. 1 shows a full-face motorcycle safety helmet (that is, a helmet which substantially fully encloses the wearer's head and face and extends around the region in front of the wearer's mouth and chin). The motorcycle helmet 1 includes the helmet main body 3, which has an opening 3a through which the rider can see, and a visor 5, which is selectively raisable and lowerable either to expose the rider's face, or to enclose the rider's face so as to deflect wind and debris.

FIG. 2 shows a cross-sectional diagram through the motorcycle helmet main body 3, indicating the typical main constructional elements thereof. The helmet main body 3 forms a layered shell which encloses a rider's head when worn. The main body 3 comprises a relatively thin rigid outer shell 10, a relatively thick layer of impact absorbing material 20 and an inner comfort layer 30. The function of the various layers is explained with respect to FIG. 3.

FIG. 3 shows diagrammatically how forces are distributed and absorbed by the various layers of the helmet during an impact. The rigid outer shell 10 deflects and distributes impact forces away from the impact point, laterally through the outer shell 10, as shown by the arrows labelled L. This dissipates the impact forces away from the point of impact, so that they are not concentrated at one point, preventing the safety helmet from splitting apart or being penetrated by the impacting object. The rigid outer shell 10 furthermore absorbs impact energy by an appropriate failure mechanism, such as splitting (cracking) or delaminating of the rigid outer shell material. The impact absorbing material layer 20 absorbs impact energy by deforming in the direction of the impact force, as shown by the arrows labelled I. The primary goal of the impact absorbing material 20, however, is to slow down movement of the wearer's head, by cushioning the forces on the wearer's head as the helmet is subjected to the impact force.

This reduces the magnitude of the force and acceleration which the brain undergoes as the impact takes place. A typical impact taking place during a motorcycle traffic accident might be the rider's head striking the concrete kerb at the side of a road. As the helmet strikes the kerb, it is brought relatively instantaneously to a halt. If the same deceleration were to be applied to the rider's head, the motorcyclist's more rigid skull would tend also to be brought promptly to a halt, whilst the softer brain matter, which has nothing holding it place, tends to continue travelling, leading to traumatic internal brain injuries. The impact absorbing material layer 20 serves as a cushioning member, giving the rider's head space and time in which to come to a halt under a more progressive deceleration, and thus hopefully avoiding serious brain injuries. The inner comfort layer 30 is provided between the impact absorbing material 20 and a user's head, to provide a comfortable tactile surface against the wearer's head when worn, and to provide softer localised padding so that the helmet will fit tightly and comfortably in place during normal use. The inner comfort layer 30 typically provides an air gap or channel to allow for ventilation around the wearer's head, and may take the form of a removable washable liner.

Motorcycle helmet design necessarily represents a trade-off between the level of safety and protection which the helmet can provide in an impact and the practicality with which the helmet can be worn when riding a motorcycle. Theoretically, the impact absorbing material 20 could be provided as a very thick construction, in one or more layers of varying degrees of density, so as to provide extensive progressive cushioning to the wearer's head during an impact. On the other hand, the helmet has to be of an overall size and shape that the motorcycle rider can wear it without undue interference from wind resistance and wind noise, and it must not be too heavy. Motorcycle helmet design has increasingly been driven towards smaller, more lightweight design, as newer materials have enabled existing safety standards to be met and surpassed with progressively more compact and lightweight configurations.

Nevertheless, despite advances in motorcycle safety helmet design, victims of motorcycle traffic accidents who wear such motorcycle safety helmets still sustain head injuries which result in brain damage. One problem in this regard is that even with rapid response times, a paramedic or other emergency medical practitioner often cannot be on the scene of the accident until some significant time after the accident has taken place. During this delay, neurological deterioration can occur, for example through bleeding into the brain, deprivation of oxygen supply, etc. The normal advice given to non-medically trained people attending motorcycle accidents is never to remove the helmet of the injured motorcycle rider, in case they may have sustained any damage to their neck or spine. During the ensuing time period, the motorcycle safety helmet tends to keep the motorcyclist's head insulated from ambient temperatures, and thus at a relatively high temperature (especially since there is no air flow through the helmet whilst the helmet is stationary). If the injured motorcyclist has sustained a head injury, this can lead to inflammation and swelling of the brain, within the skull and helmet. Often, the head can swell up inside the motorcycle safety helmet, making it difficult or impossible to remove the helmet, after a certain period of time has elapsed (the helmet can then not be removed until the injured motorcyclist arrives at a hospital, where specialist cutting tools, such as those normally used for removing plaster casts, can be used to cut the helmet away from the motorcyclist's head). These conditions can promote neurological deterioration, before any significant medical attention can be administered.

It would therefore be desirable to provide means by which the onset of brain damage can be inhibited in a motorcycle accident victim.

United States patent publication U.S. Pat. No. 5,950,234 A1, to Leong et al, discloses a cooling pack head covering. The cooling pack is intended to be worn so as to cover the scalp of a patient undergoing chemotherapy treatment. It is contemplated that the cooling pack may be a chemical cold pack, in which chemicals in a container become cold when they are mixed together by breaking a barrier which otherwise separates them. The cooling pack is generally circular and has a "V" shaped notch formed therein to enable the pack to be wrapped around and secured to a patient's head, in a generally bowl shape. It is contemplated that, if an American football helmet were to be used, then the cooling pack might be formed in multiple parts to fit in the helmet, with the objective of cooling the wearer's scalp to a temperature which will minimise hair loss. The cooling pack must be activated before being put on, and has no means by which to activate the cooling pack whilst being worn.

Further United States patent publication U.S. Pat. No. 5,469,579 A1, to Tremblay et al, discloses a head cooling device for mounting over a person's head, generally within headgear or a safety helmet, such as the construction hats worn on building sites. The head cooling device is configured to sit within the hat or helmet of a wearer, and to contain ice cubes therein. As the ice cubes melt, the head cooling device allows the melting water to pass one drop at a time onto the wearer's scalp, so as to absorb and extract heat from the wearer's head.

US patent publication U.S. Pat. No. 5,755,756 A1, to Freedman, Jr. et al, discloses a hypothermia-inducing resuscitation unit which includes a helmet adapted to be mounted on the head of a patient. A coolant source is pumped from external of the helmet into a bladder which is inflatable to achieve a tight fit over the head of a patient, and to provide cooling to the patient's head.

SUMMARY OF THE INVENTION

According to a first aspect of the present invention, there is provided headwear comprising an endothermic reactor and a trigger to initiate an endothermic reaction in the reactor whilst being worn on a wearer's head.

Preferably, the trigger is arranged to initiate the endothermic reaction in response to detection of an impact or imminent impact on the headwear. Alternatively or in addition thereto, the trigger is arranged to initiate the reaction in response to an impact on the headwear.

In preferred embodiments, the headwear is a helmet for protection of a wearer's head from impacts. Most preferably, the headwear is a motorcycle safety helmet. The headwear may comprise means to detect an impact or imminent impact based on a detected acceleration of the headwear exceeding a threshold magnitude. Preferably, then, the trigger is arranged to initiate the reaction in response to a force or pressure generated in the headwear by the impact exceeding a threshold magnitude.

In further preferred embodiments of the headwear, the endothermic reactor comprises two or more reagents which will react together in an endothermic reaction, when the reaction is initiated. Each of the two or more reagents may be contained in the endothermic reactor, separated from other reagents with which it will react, in respective cells or reservoirs. In certain preferred embodiments, at least one of the reagents is contained in a layer arranged to encompass substantially all or a part of the head of a wearer. One or more membranes may separate the reagents from each other, the trigger being configured to initiate the endothermic reaction by opening a hole in the membrane through which the separated reagents may be brought into contact. In one form, the trigger includes a plunger for opening the hole in the membrane. In another form, the trigger includes one or more frangible regions in the membrane, configured to open to form a hole when tension in the membrane exceeds a threshold magnitude. In one more form, the membrane or trigger comprises a shape memory alloy, or a shape memory structure, in a first memorized state and is configured to open a hole in the membrane in response to a change in the shape memory state to a second memorized state.

In yet further preferred embodiments, the trigger comprises a shape memory alloy, or a shape memory structure, in a first memorized state and is configured to initiate the reaction in response to a change in the shape memory state to a second memorized state.

In even further preferred embodiments, the trigger comprises an element of electroreactive material for initiating the reaction in response to a signal generated by said detection.

In still further preferred embodiments, the endothermic reactor is configured to contain the reagents and the reaction products of the endothermic reaction prior to and during the reaction.

Preferred embodiments of the headwear further include an emergency initiation device also operative to initiate the reaction.

According to a second aspect of the present invention, there is provided headwear comprising a gas-expansion cooling device for cooling a wearer's head and a trigger to initiate release of the gas from a pressurized container into a decompression region adjacent to or in a region of the headwear that is configured to enclose the head of a wearer.

According to a third aspect of the present invention, there is provided headwear comprising a reagent package arranged to remove heat energy from a wearer's head when activated by an impact.

According to a fourth aspect of the present invention, there is provided a motorcycle safety helmet comprising: a rigid outer shell; a layer of impact absorbing material inside the rigid outer shell; an endothermic reactor, substantially contained inside the rigid outer shell, containing two or more reagents which will react together in an endothermic reaction to absorb heat from inside the helmet; and a trigger arranged to initiate the endothermic reaction in the reactor, whilst being worn on a wearer's head, in response to detection of an impact or imminent impact on the helmet.

According to a fifth aspect of the present invention, there is provided a motorcycle safety helmet comprising: a rigid outer shell; a layer of impact absorbing material inside the rigid outer shell; an endothermic reactor, substantially contained inside the rigid outer shell, containing two or more reagents which will react together in an endothermic reaction to absorb heat from inside the helmet; and a trigger arranged to initiate the endothermic reaction in the reactor, whilst being worn on a wearer's head, in response to an impact on the helmet.

In preferred embodiments of the motorcycle safety helmet of the fourth or fifth aspect, each of the two or more reagents is contained in the endothermic reactor, separated from other reagents with which it will react, in respective cells or reservoirs. At least one of the reagents may in that case be contained in a layer arranged to encompass substantially all or a part of the head of a wearer. Preferably, one or more membranes separate the reagents from each other, the trigger being configured to initiate the endothermic reaction by opening a hole in the membrane through which the separated reagents may be brought into contact.

The headwear of the present invention is able to be configured to be carried with the first aid kit of any paramedic, and can be used to provide cooling to the brain of an accident victim whilst awaiting arrival of transport to a hospital, and during the journey thereto. Headwear according to the present invention may also find application for providing cooling to the brains of patients after arrival or who have already been received in a hospital.

A motorcycle safety helmet which includes, incorporates or embodies headwear according to the present invention is able to provide significant cooling to the brain of a motorcycle accident victim without the need to remove the motorcycle rider's helmet. Neurological deterioration may thereby be reduced and brain damage can be avoided. It is furthermore thereby possible to reduce the tendency for the motorcyclist's head to overheat or become swelled up whilst it remains within the confines of the motorcycle helmet.

BRIEF DESCRIPTION OF THE DRAWINGS

To enable a better understanding of the present invention, and to show how the same may be carried into effect, reference will now be made, by way of example only, to the accompanying drawings, in which:

FIGS. 12A to 12C are a series of diagrammatic views illustrating the principle of operation of a further trigger suitable for use in conjunction with the foregoing embodiments of the present invention;

FIGS. 13A to 13C are a series of diagrammatic views showing a further triggering system suitable for use in the foregoing embodiments of the present invention;

DETAILED DESCRIPTION

Figure 1:
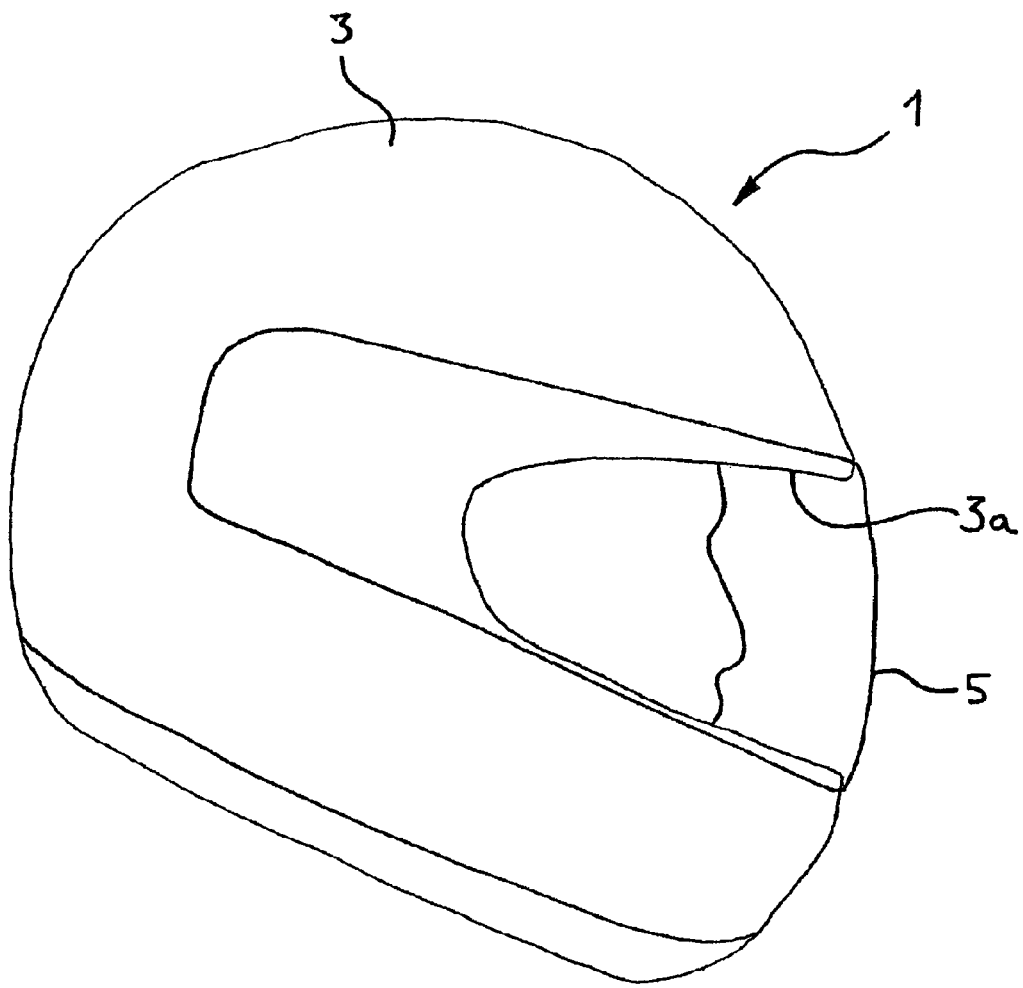
FIG. 1 is a side external view showing diagrammatically the main components of a typical full-face motorcycle safety helmet.

In the following, like reference numerals are utilised are used to indicate the same or similar features in the various embodiments of the invention.

In the following, it will be appreciated that acceleration generally encompasses both a positive acceleration, which increases speed, as well as a negative acceleration (deceleration), by which speed is reduced. The terms acceleration and deceleration as used herein should thus be considered as being interchangeable and mutually encompassing, unless the specific context dictates otherwise.

Figure 4:
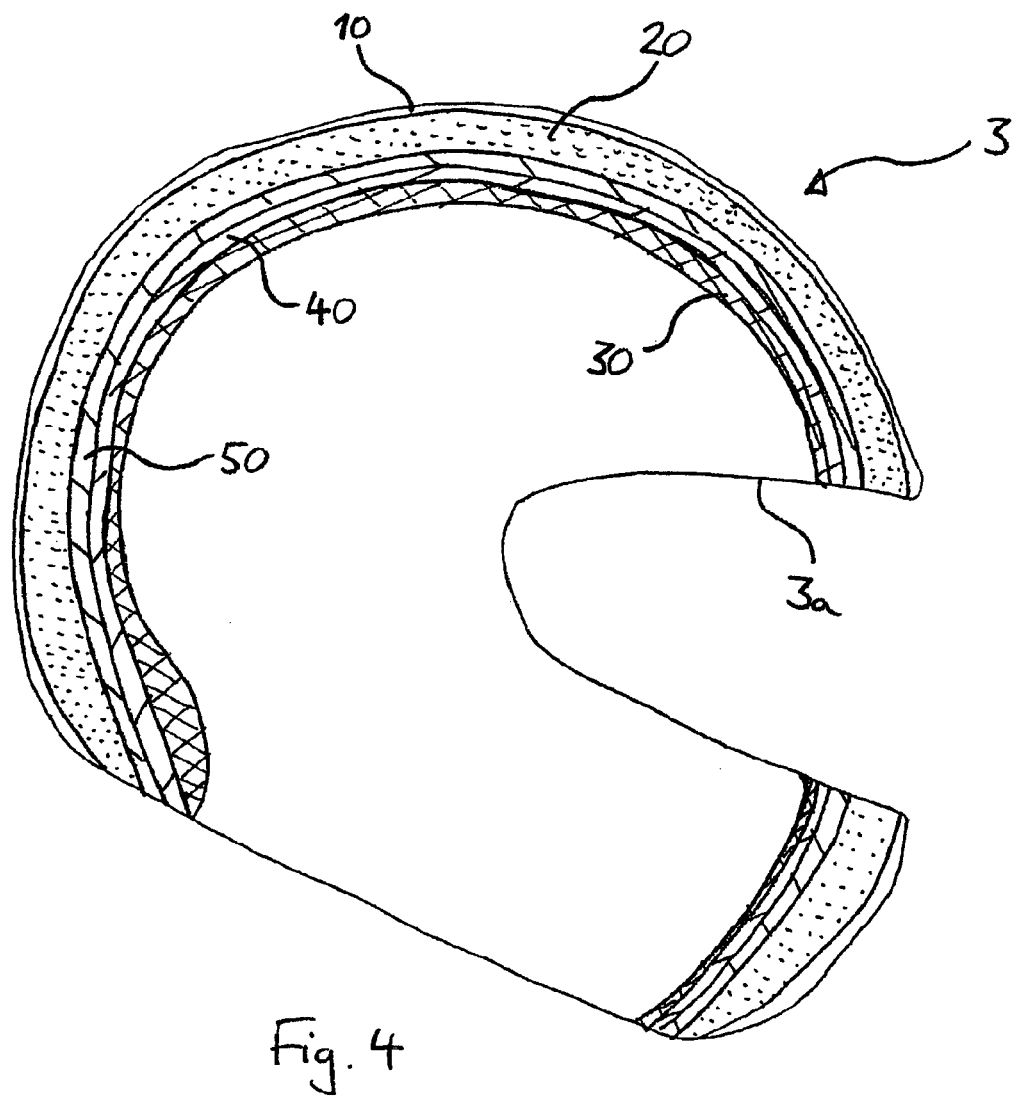
FIG. 4 shows a cross-sectional side view of an embodiment of the main body of a motorcycle safety helmet according to the present invention.

A first embodiment of the main body 3 of a motorcycle safety helmet is illustrated diagrammatically in FIG. 4, which details the main constructional elements of the motorcycle helmet main body 3.

Figure 2:
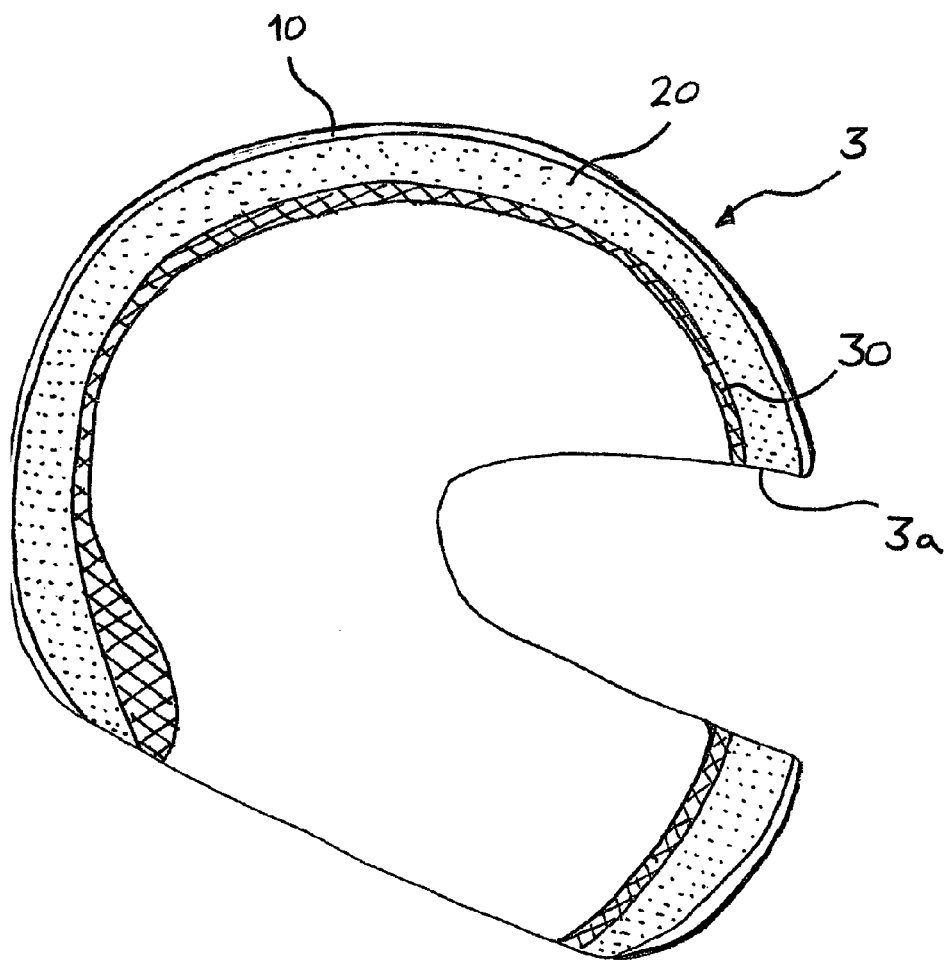
FIG. 2 is a cross-sectional side view, showing a diagrammatic representation of the key constructional elements of a motorcycle safely helmet main body.

Similarly to the known motorcycle safety helmet described above with reference to FIGS. 1 to 3, the motorcycle safety helmet main body 3 includes a rigid outer shell 10, inside which is provided an impact absorbing material layer 20. An inner comfort layer 30 is furthermore arranged within the interior of the motorcycle safety helmet main body 3, to provide a contact surface with the head of a wearer of the motorcycle safety helmet.

It will be appreciated that although the illustrated embodiments of the motorcycle safety helmet of the present invention are illustrated as full-face safety helmets, other known forms of motorcycle safety helmet may be adapted to incorporate a suitable endothermic reactor and triggering device, according to the principles set forth herein. Specifically, endothermic reactors and triggering devices arranged in accordance with the principles of the present invention may be applied to so-called open-face or three-quarter helmets, which still provide protection over the ears of a wearer but leave the lower face and chin exposed; half-helmets, which provide protection only to the top of the wearer's head; and flip-face helmets, which have a flip-up chin bar and visor, allowing the helmet to convert between a full-face configuration and an open-face configuration.

The rigid outer shell 10 is typically 3 to 5 mm thick and is normally either an injection-moulded thermoplastic or a pressure-moulded thermoset reinforced with glass or Kevlar fibres. Polycarbonate outer shells are widely used. The specific material and type of construction selected for the rigid outer shell is, however, not critical to achieving the advantages obtainable with the present invention. The outer shell 10 not only distributes and absorbs energy by bending and failing at the impact point, but also serves to retain the impact absorbing material layer 20 during an impact event, thus preventing it splitting apart and separating from its protective position on the wearer's head.

The impact absorbing material layer 20 is typically formed of a polystyrene bead moulding, with a density in the range 40 to 70 kg/m$^3$. The foam cells are closed, so the air inside them is compressed during an impact. Advantageously, the polystyrene or expanded polystyrene absorbs a lot of energy as it is crushed (up to 90% of its original thickness is typical), but does not store the energy and rebound like a spring, instead retaining its deformation (remaining compressed or crushed). This prevents the stored energy bouncing back and striking against the wearer's brain for a second time. Polyurethane foam has also been used as the impact absorbing material layer 20 in some helmets.

The human brain basically floats inside the skull, within a bath of cervical-spinal fluid and a protective cocoon called the dura. As noted above, during a severe impact the skull can be brought to a stop, or otherwise accelerated, very suddenly, but the brain continues moving, which can lead to a number of different brain injuries, from shearing of the brain tissue to bleeding in the brain, bleeding between the brain and the dura, or bleeding between the dura and the skull. Any such injury tends to lead to inflammation and swelling of the brain within the skull, which in normal circumstances cannot occur due to the confined nature of the brain within the rigid skull. (In a hospital environment, build up of pressure and swelling of the brain within the cranial cavity can be relieved by drilling or cutting-open the skull to relieve the internal pressure.) The layer of impact absorbing material 20 has the function of gradually decelerating the skull during an impact event, so as to minimise differences in motion between the skull and the brain.

The inner comfort layer 30 is provided usually as a combination of soft padding and a breathable mesh, to ensure that the motorcycle safety helmet is a comfortable fit during normal use, and to ensure that it is held appropriately in place on the user's head, to prevent the helmet from moving around and interfering with the concentration and vision of the motorcyclist.

The motorcycle safety helmet main body 3 illustrated in FIG. 4 includes an endothermic reactor, formed in this embodiment of two adjacent layers between the inner comfort layer 30 and the impact absorbing material layer 20. More or fewer layers may be used, depending on the preferred reactor arrangement for any particular application. The endothermic reactor in FIG. 4 is formed by an inner layer 40 and an outer layer 50. These two layers contain two distinct reagents, which, when mixed together, undertake an endothermic reaction. For the present purposes, a reaction need not require a change in the electron state of the substances in each layer, but may be simply the dissolution of one substance into a quantity of the other substance. It is presently preferred for the outer layer 50 to contain a volume of water, and for the inner layer 40 to contain an amount of ammonium nitrate.

During normal use of the motorcycle safety helmet 3, the two reagents are held separated from one another in their respective layers. The endothermic reactor is configured to initiate a reaction between the substances in the inner layer 40 and outer layer 50, as a result of the helmet suffering an impact, by operation of an appropriate trigger mechanism (not shown in FIG. 4). The endothermic reaction taking place between the substances in the two layers 40 and 50 absorbs energy from the head of the wearer of the motorcycle safety helmet.

When the endothermic reactor is triggered, the water in outer layer 50 is released into the inner layer 40, to initiate the endothermic reaction by causing the ammonium nitrate to begin to dissolve into the water. This immediately begins to produce a cooling effect within the interior of the motorcycle safety helmet. The reaction between water and ammonium hydrate is able to deliver an amount of cooling corresponding to around 1° C. per minute after the reaction is initiated, resulting in noticeable cooling after around four minutes. Because the endothermic reaction is progressive, heat will be continually absorbed from the head and brain of the motorcycle helmet wearer during the endothermic reaction. The progressive nature of the reaction can be enhanced by configuring the outer layer 50 containing the water to release the water into the layer containing the ammonium nitrate in a gradual fashion, such as through restricted openings or via capillary action. The ongoing release of the one reagent into the other will lead to an ongoing cooling effect for an extended period of time, although this will be determined also in part by the quantity of the reagent materials contained in the helmet main body 3, in the inner layer 40 and outer layer 50.

Of course, the endothermic reaction should not be so severe as to cause any cold burning to the patient, and in this respect the inner comfort layer 30 can provide a useful heat transfer medium between the endothermic reactor (consisting of the inner layer 40 and outer layer 50) and the head of the wearer of the motorcycle helmet.

A dissolution reaction between water and ammonium nitrate is presently preferred, since the reagents and the products of the reaction are relatively non-toxic. It is, of course, intended for the reagents to remain contained within the endothermic reactor, and not to be released onto the wearer or into the external environment. Nevertheless, it is conceivable that the reagents could be released during the impact event, exposing the wearer of the motorcycle safety helmet to the reagents and/or products. The reagent and reaction products should, for this reason, not be toxic to the wearer of the motorcycle helmet or any attending medical practitioner, if they became exposed to them. As well as dissolution of ammonium nitrate in water, a number of further endothermic reactions are known which could be of practical application, in accordance with the present invention. Notably, for applications where the headwear in question is not a motorcycle safety helmet, there is a markedly reduced risk of the wearer of the headwear coming into contact with the reagents and reaction products in question. Other known endothermic chemical reactions, which might be utilised in place of dissolving ammonium nitrate in water, are:

reaction of barium hydroxide octahydrate crystals with dry ammonium chloride;
dissolving ammonium chloride in water;
reaction of thionyl chloride ($SOCl_2$) with cobalt (II) sulfate heptahydrate;
mixing water with potassium chloride; and
reaction of ethanoic acid with sodium carbonate.

It is also contemplated that in an alternative configuration the endothermic reactor might contain pressurized or liquefied gas, which could be gradually released into the interior of the helmet, between the impact absorbing material 20 and the inner comfort layer 30, so as to provide cooling to the inside of the helmet as the gas expands. The gas expansion passage within the helmet could be appropriately configured so as to vent the expanded gas into the atmosphere after release and cooling of the helmet interior. Such form of cooling would, however, be more appropriate for alternative items of headwear than a motorcycle safety helmet, which is liable to suffer extreme impacts, as well as substantial temperature variations. Such gas expansion cooling, however, might find ready application to a headwear item suitable for use by paramedic teams in the initial treatment of head injury victims.

The cooling of the internal region of the helmet not only provides immediate commencement of the cooling process during an impact event, but offers the significant advantage, in a motorcycle safety helmet application, of providing cooling to the motorcyclist's head without having to remove the motorcycle safety helmet. It is advisable not to move the victim of a motorcycle traffic accident, if safe and reasonable not to do so, in case they have suffered spinal or neck injuries. If they have, attempting to move the accident victim or to remove the motorcycle safety helmet could result in causing damage to the spinal column; motorcycle safety helmets should only be removed once an experienced medical practitioner has had opportunity to assess whether it is safe to remove the helmet. By providing cooling to the inside of the motorcycle safety helmet, the onset of neurological deterioration following the initial brain trauma can be delayed and the chances of suffering brain damage reduced. Similarly, the consequences of further injuries, for example, restricted blood flow and lack of oxygen to the brain, can also be offset by cooling of the brain in this fashion. Additionally, swelling and inflammation can be reduced, which will relieve pressure on the brain within the skull cavity, as well as ensuring that it should be possible still to remove the motorcycle safety helmet from the wearer's head, at an appropriate time.

Figure 5:
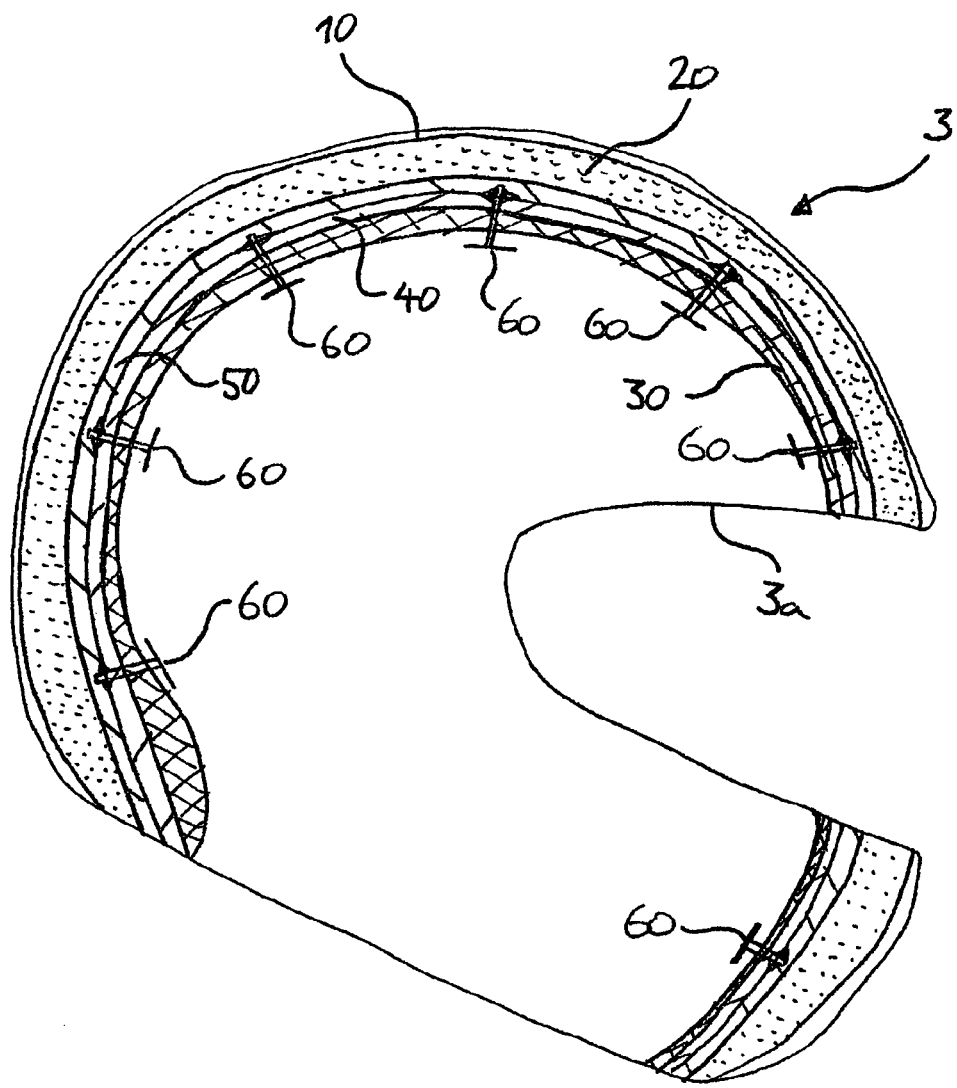
FIG. 5 shows a cross-sectional side view of a second embodiment of the main body of a motorcycle safety helmet according to the present invention.

FIG. 5 shows a second embodiment of a motorcycle safety helmet main body 3, including the same reactor inner layer 40 and reactor outer layer 50 as shown in FIG. 4. In the embodiment of FIG. 5, multiple plungers 60 are provided as trigger mechanisms by which to initiate the endothermic reaction between the inner layer 40 and outer layer 50. The plunger trigger mechanism 60 is configured so that, during the contact expected in normal use between the head of the motorcyclist and the plunger, no triggering action will take place. However, during an impact situation, the forces applied by the user's head against the sides of the helmet will cause the plungers 60 to be depressed, initiating the reaction between the substances in the inner layer 40 and outer layer 50.

Figure 6:
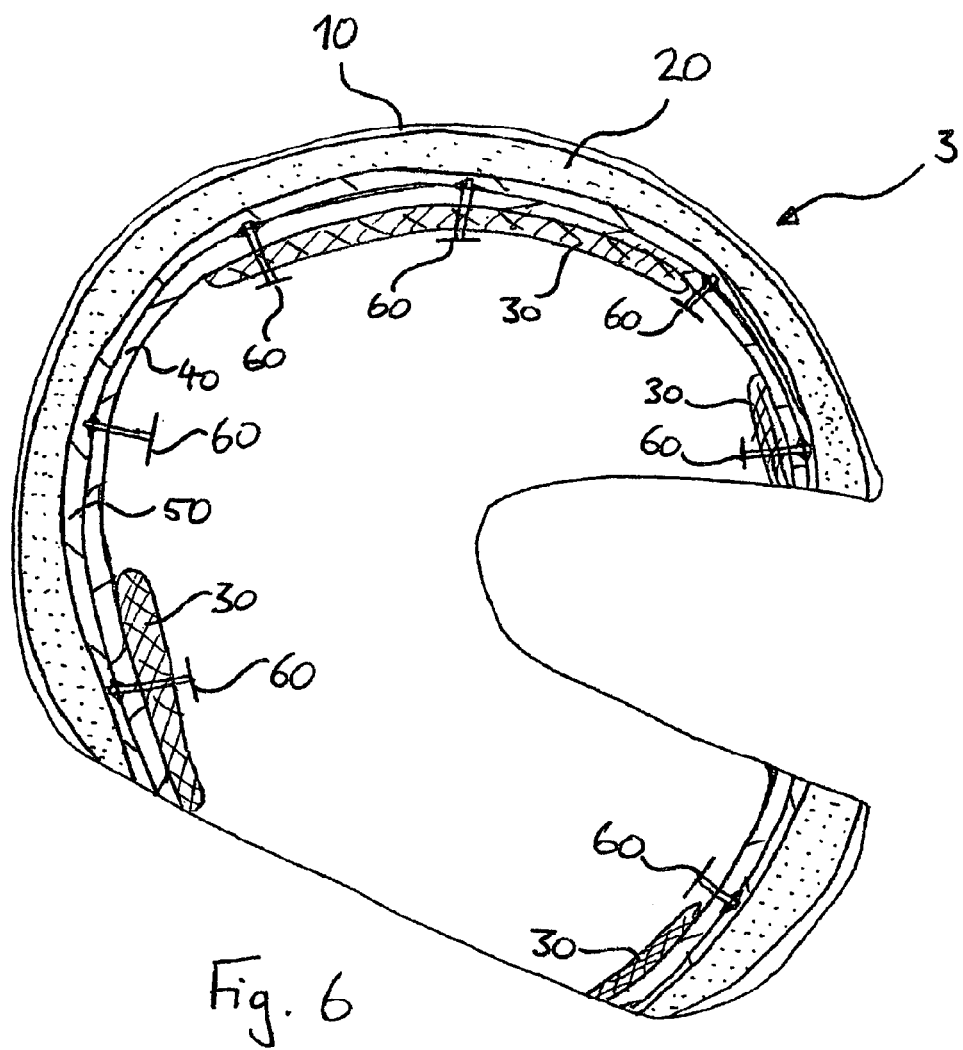
FIG. 6 shows a cross-sectional side view of a third embodiment of the main body of a motorcycle safety helmet according to the present invention.
Figure 7:
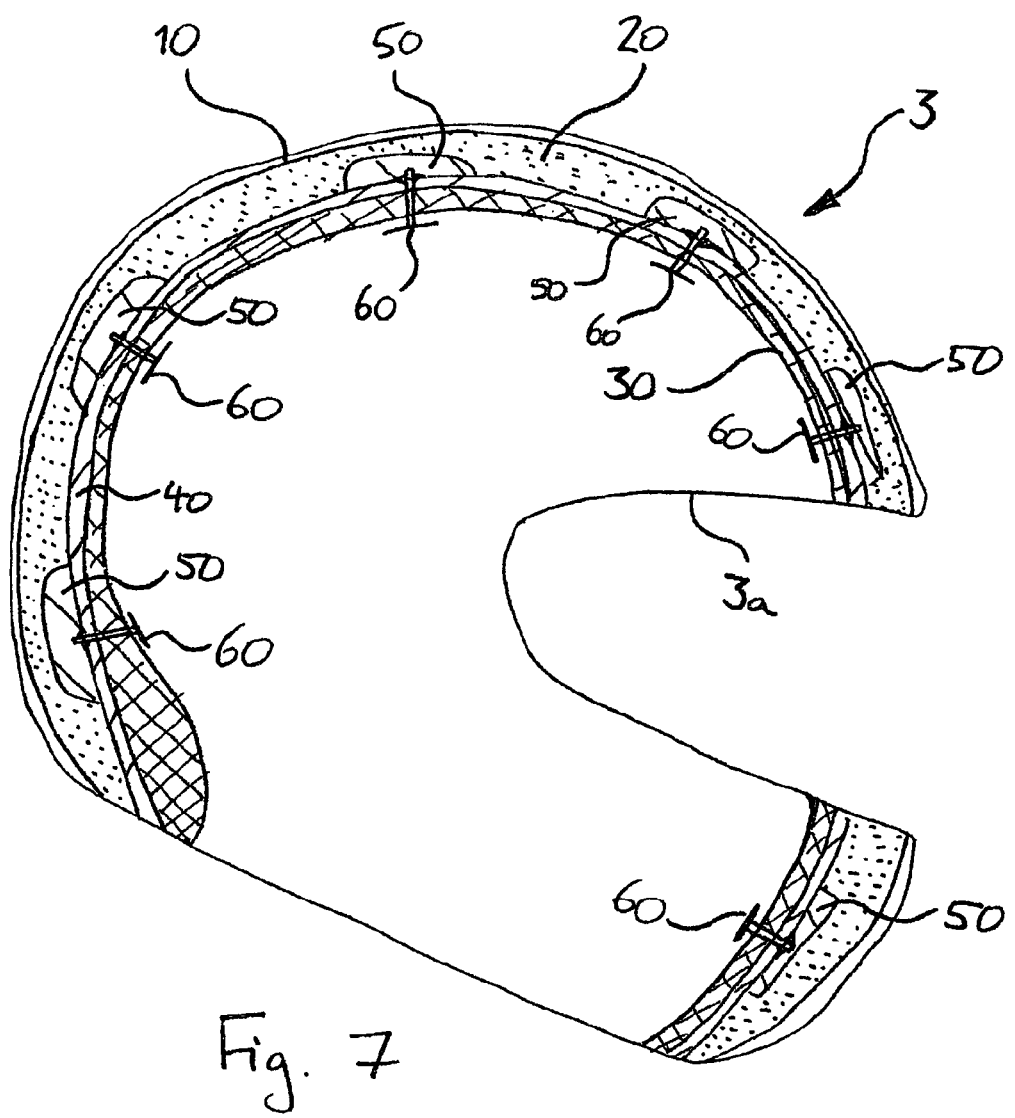
FIG. 7 shows a cross-sectional side view of a fourth embodiment of the main body of a motorcycle safety helmet according to the present invention.
Figure 8:
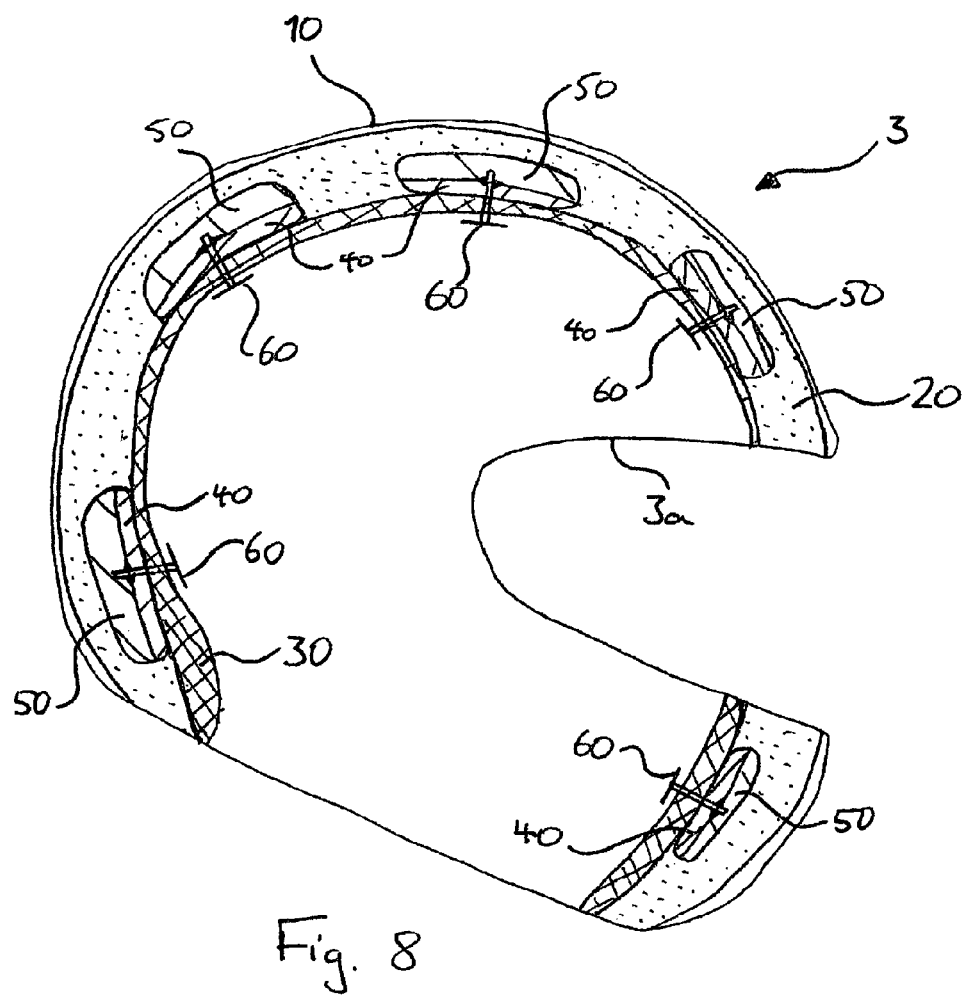
FIG. 8 shows a cross-sectional side view of a fifth embodiment of the main body of a motorcycle safety helmet according to the present invention.

FIGS. 6 to 8 show alternative configurations of how the inner comfort layer 30, inner reactor layer 40 and outer reactor layer 50 may be arranged so as to be better accommodated, comfortably, within the confines of the motorcycle safety helmet.

It is of course recognised that the endothermic reactor layers 40 and 50 increase the overall mass and bulk of the motorcycle safety helmet main body 3. However, it is not uncommon for the impact absorbing material layer 20 to have a relatively complex structure in existing motorcycle safety helmets (the structure may be arranged as a series of segments or other components, similar to the helmets worn by pedal cyclist, or can be made up of separate components having different densities for different impact absorbing characteristics). This provides significant scope for forming the impact absorbing material into a non-uniform layer surrounding the head of the wearer of the motorcycle safety helmet, by which expedient various cavities and channels can be formed in the impact absorbing layer 20 within which the materials of the endothermic reactor can be stored in their separate inner layer 40 and outer layer 50. The endothermic reactor may be provided thus as a single endothermic reactor comprising two layers which each substantially fully surround the wearer's head, or as one or several separate reactors or reactor units comprising respective or communal inner and outer layers of reagent.

The embodiment shown in FIG. 6 is similar to that in FIG. 5, except that the inner comfort layer 30 is provided only as a series of separate comfort pads within the inner region of the motorcycle safety helmet main body 3.

In the embodiment of FIG. 7, the helmet is provided with an inner comfort layer 30 and an inner reactor layer 40, similar to the embodiments of FIGS. 4 and 5. However, the outer reactor layer 50 is formed as a series of pockets or cells containing the second reagent (water), each configured with a trigger (plunger) 60 to release the water into the ammonium nitrate layer during an impact event. As can be seen, the outer layer 50 is formed into various pockets of reagent located within the material of the impact absorbing layer 20, spaced around the shell of the helmet main body 3.

Although these pockets may be formed as separate cells or reservoirs, they may be fluidly interconnected by suitable channels. In the embodiment of FIG. 7, the separate outer reagent reservoirs 50 feed into a common reactor inner layer 40.

A similar arrangement is shown in FIG. 8, in which pockets are formed within the material of the impact absorbing layer 20, within which respective ones of both an inner layer 40 and an outer layer 50 of reagent are formed, thus constituting several individual reactors in the different pocket locations. In the example of FIG. 8, a separate trigger or plunger 60 is provided for each of the individual reactor pockets.

Figure 3:
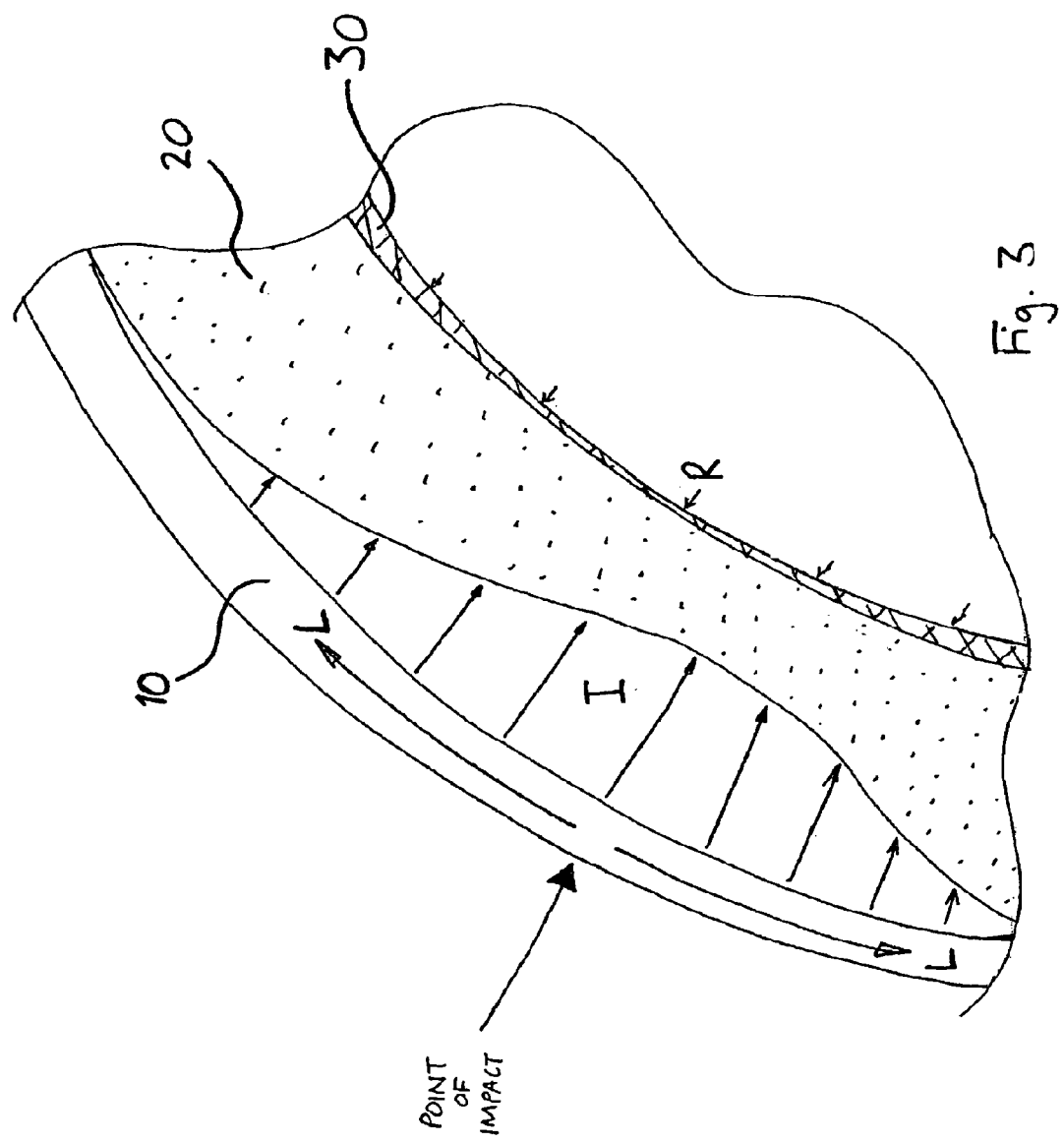
FIG. 3 is an enlarged cross-sectional view of a portion of the motorcycle main body of FIG. 2, indicating diagrammatically the manner in which forces are distributed and absorbed in the motorcycle safety helmet during an impact.
Figure 9:
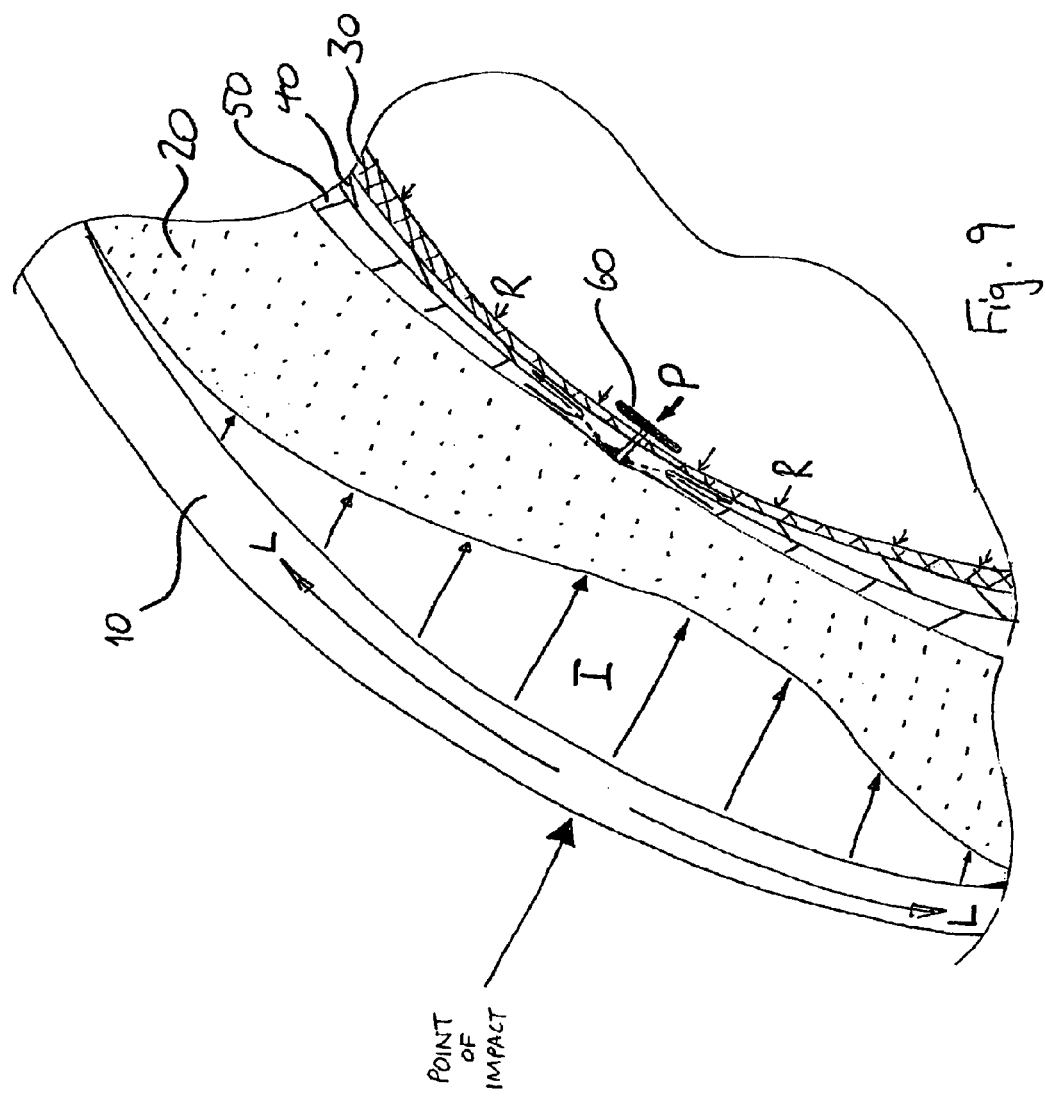
FIG. 9 is an enlarged view of a cross-section through a portion of the main body of the motorcycle safety helmet according to the present invention, indicating diagrammatically how the foregoing embodiments of the motorcycle safety helmet can function in the event of an impact.
Figure 10:
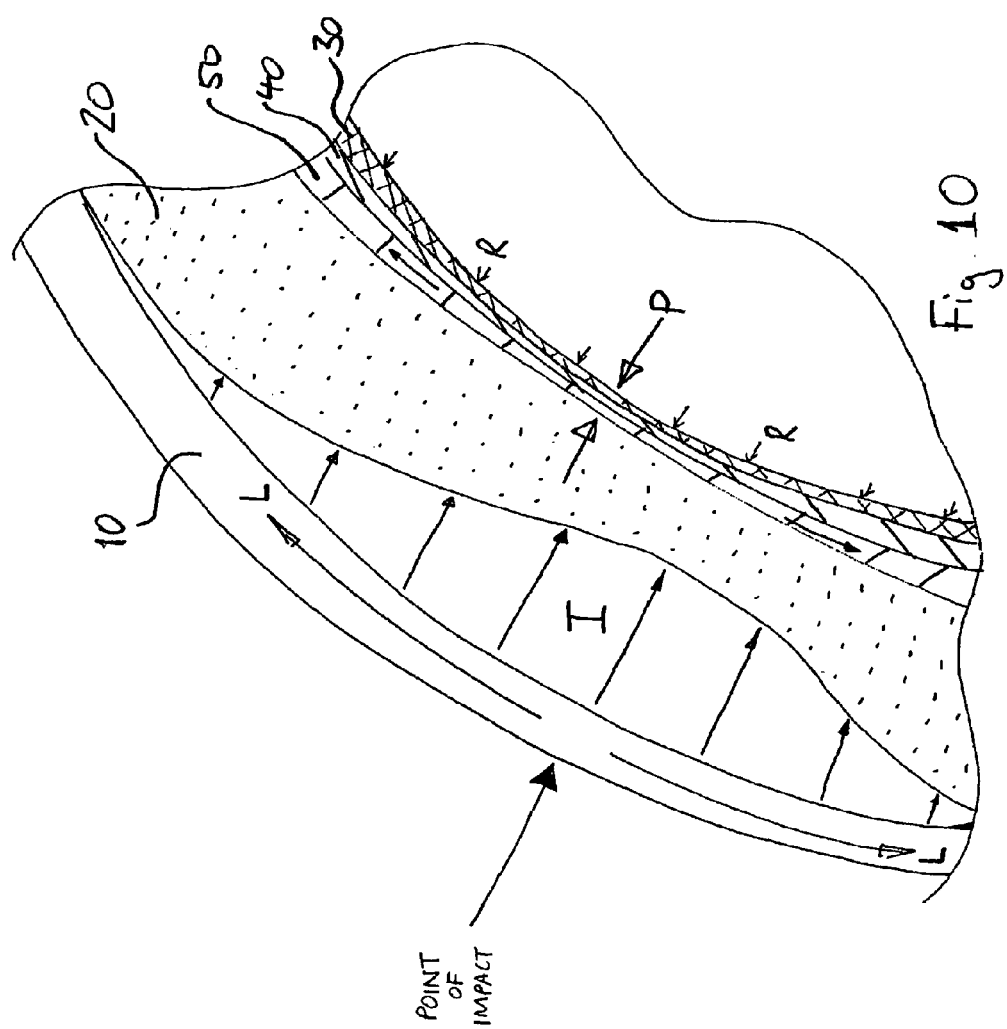
FIG. 10 is a further enlarged cross-sectional view showing a portion of the main body of a motorcycle safety helmet according to the present invention, showing diagrammatically the effect an impact may have on the foregoing embodiments of the motorcycle safety helmet.

Drawings FIG. 9 is a schematic enlarged cross-sectional view showing one example of how the plunger 60 can be depressed during an impact event equivalent to that shown in drawings FIG. 3. Once the plunger 60 has been depressed and the reaction has been initiated, the water in the outer reactor layer 50 can flow freely into the inner reactor layer 40, as denoted by arrows in FIG. 9. FIG. 10 similarly illustrates how the adjacent layers of the reactor are compressed together at a compression point P, between the outer impact absorbing layer 20 and the inner comfort layer 30, as the wearer's head travels into and decelerates against the impact absorbing material layer 20 (or vice versa). In the case of water being contained in the outer layer 50, this water is compressed and forced outwardly away from the compression point P, during the impact event.

Any suitable trigger mechanism can be utilised for initiating the endothermic reaction between the inner layer 40 and outer layer 50. Several examples follow which can be classified as "passive", the reaction being initiated simply by virtue of the compression of the inner and outer layers 40,50 between the impact absorbing material 20 and the head of the wearer of the motorcycle safety helmet. Alternatively, "active" trigger mechanisms could be employed, which provide a further input to initiate the endothermic reaction, in response to a signal generated as a result of the impact event, or detection of a likely impact event. For example, accelerometers can be used to determine when the helmet undergoes acceleration having a magnitude above a specified threshold, indicative of a collision or impact. Such sensors can operate from a separate battery or other power source self-contained within the helmet, or may be powered via the existing battery supply of a motorcycle. These and similar trigger mechanisms already exist for use in "pre-emptive" (i.e., those designed to trigger an action immediately prior to an impact) motorcycle safety applications. For example, various applications are presently being developed by which to incorporate airbag features into motorcycle safety helmets and other motorcycle clothing, and this line of development may be utilised in conjunction with the endothermic reactors of the present invention.

Figure 11:
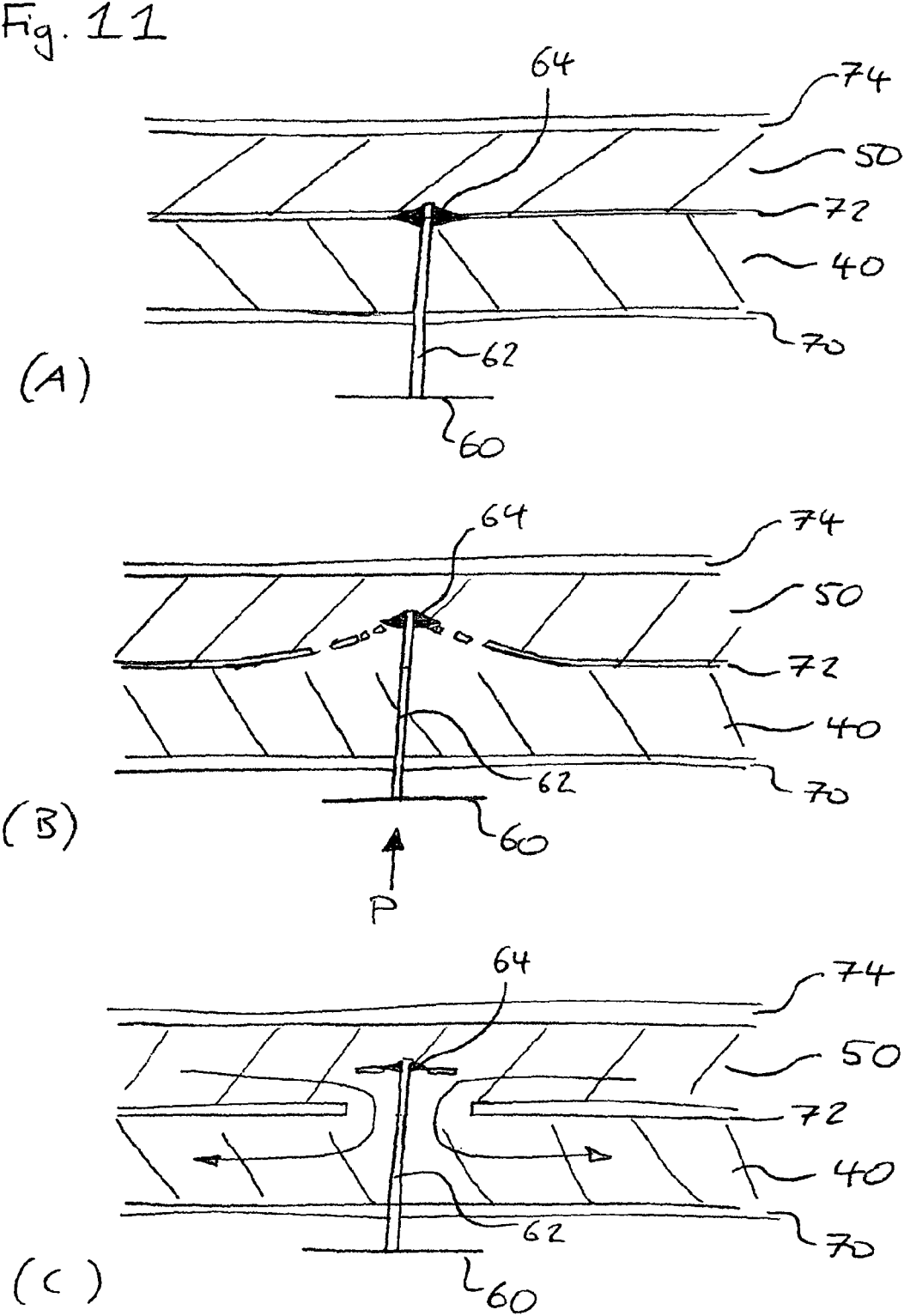
FIGS. 11A to 11C are a series of diagrammatic views illustrating a principle of operation of a trigger unit for use in conjunction with the foregoing embodiments of the present invention.

A first illustrated triggering mechanism is shown in FIGS. 11A to 11C. As shown in FIG. 11A, the endothermic reactor is formed by inner layer 40 and outer layer 50, which are separated by an intermediate membrane 72. Encapsulating membranes 70 and 74 are provided respectively inside and outside the inner and outer layers 40 and 50 of the reactor, to contain the reagents within the respective layers. Plunger 60 is connected via a shaft 62 to a plug 64 formed in intermediate separating layer 72 of the endothermic reactor. Plunger 60 initially protrudes internally of the inner membrane 70, as shown in FIG. 11A. During an impact event, the compression force at point P forces the plunger 60 into the outer layer 50, and causes plug 64 to separate from the adjacent portions of the separating membrane 72, as it is forced outwardly by the shaft 62 being depressed. This is shown schematically in FIG. 11B.

After the impact event, the plunger 60 remains depressed, with the plug forced into the outer reactor layer 50. As shown in FIG. 11C, this allows the reagent (water) stored in outer layer 50 to flow into the inner layer 40 (or vice versa, if the layer in which each reagent is stored is reversed).

A further trigger mechanism is illustrated in FIGS. 12A to 12C. The trigger mechanism comprises a plunger 80, with a pointed shaft 82 extending into the inner layer 40 of the reactor. A biasing member, here in the form of a spring 84, is provided between the plunger 80 and the membrane 70 of the endothermic reactor, and biases the plunger 80 inwardly into the motorcycle safety helmet cavity, against a spring plate 86, as shown in FIG. 12A.

During an impact event, as shown in FIG. 12B, the plunger 80 becomes depressed, causing the pointed shaft 82 to pierce the separating membrane 72 between the inner layer 40 and outer layer 50 of the endothermic reactor. At the same time, this compresses the spring 84 between the plunger 80 and spring plate 86.

After the impact event, the spring 84 produces a spring force S, which biases the plunger 80 inwardly into the interior of the helmet. This serves to retract the pointed shaft 82 from the separating membrane 72, as the spring force acts against the spring plate 86. This again allows the reagent (water) in the outer layer 50 to flow into the inner layer 40, to initiate the endothermic reaction.

A further alternative trigger arrangement is shown in FIGS. 13A to 13C, in which the outer layer 50 can be seen to be divided into separate cellular elements between dividing membranes 76, and between the separating membrane 72 and the outer membrane 74. The separating membrane, as shown in FIG. 13A is provided with frangible regions 78, which are deliberately weakened relative to the remainder of the membrane layer, and configured to tear or burst when a tension in the separating membrane 72 exceeds a predetermined value (i.e., when the pressure within the cell, which produces a tension in the membrane 72, exceeds a predetermined value).

FIG. 13B illustrates how the inner and outer reactor layers are compressed during an impact event, displacing the reagent in the outer layer 50 away from the impact point, and increasing the pressure in that cell. This causes frangible regions 78 to burst under the increased pressure, thus releasing the reagent (water) from the cell in the outer layer 50 into the inner layer 40, thereby initiating the endothermic reaction, as shown in FIG. 13C. As also visible in FIG. 13C, the membrane 72 separating the inner layer 40 and outer layer 50 is provided under substantial initial tension, such that, when the frangible regions 78 are burst, the membrane shrinks away from the newly created holes, widening the available area through which the reagent in the outer layer 50 can pass into the inner layer 40.

Figure 14:
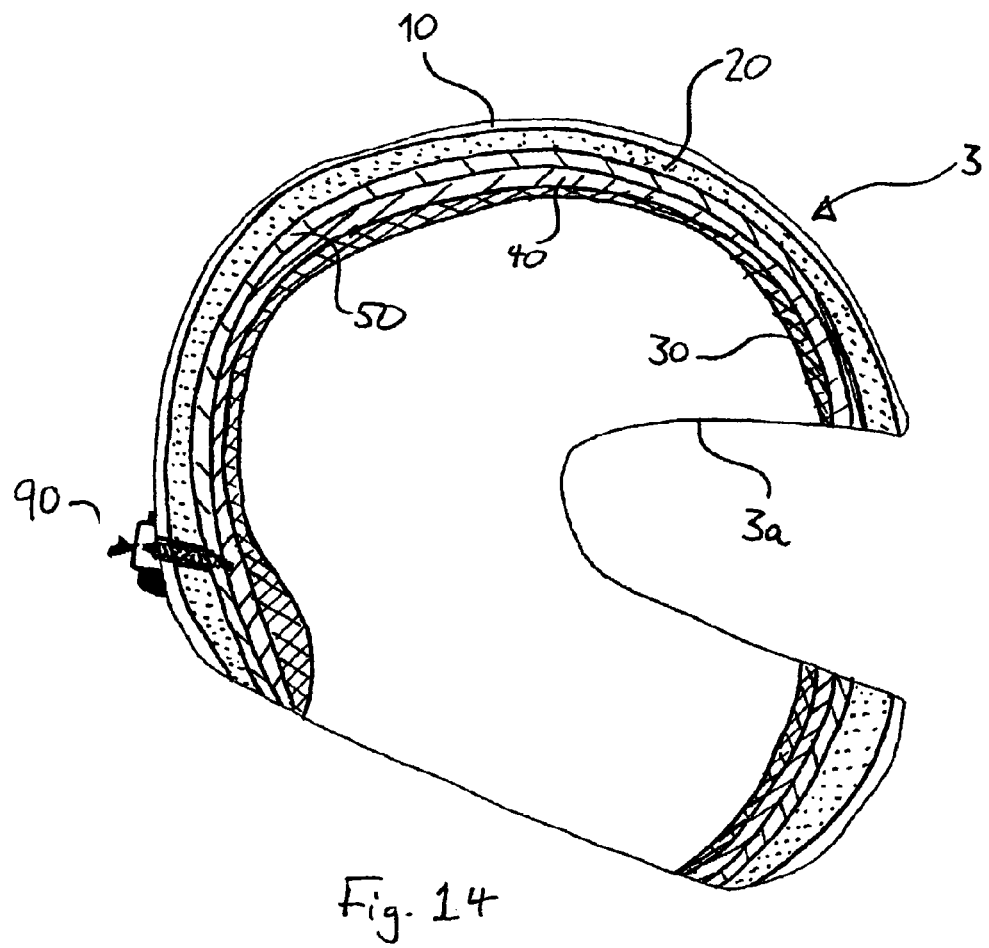
FIG. 14 is a cross-sectional side view of an embodiment of the main body of the motorcycle safety helmet according to the present invention, indicating a 14 further optional feature which may be applied to any of the foregoing embodiments of the invention.
Figure 14A:
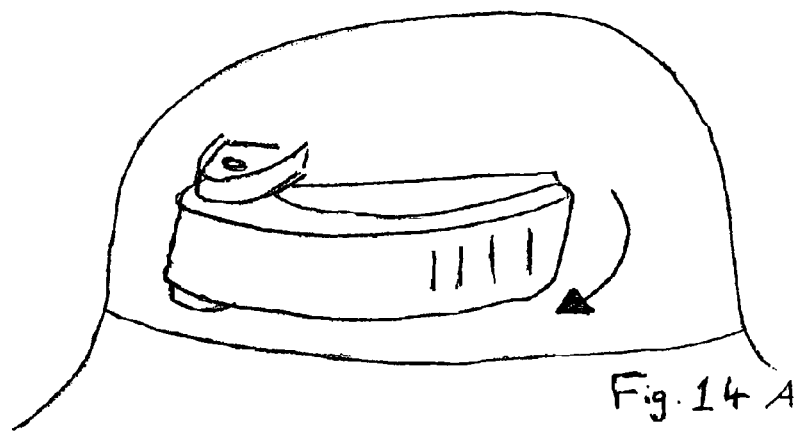
FIG. 14A shows a close-up perspective view of the further optional feature of FIG. 14.

FIG. 14 shows an embodiment of the main body 3 of a motorcycle safety helmet according to the present invention, including the same rigid outer shell 10, impact absorbing material layer 20 and inner comfort layer 30, as well as inner and outer reactor layers 40 and 50, as shown in the foregoing embodiments. The helmet main body 3 further includes an emergency initiation switch, through which the cooling effect of the helmet can be deployed by another person. This allows any person first on the scene of a motorcycle traffic accident to initiate the reaction, to ensure that the cooling process has commenced. Emergency initiation device 90 can take any suitable form, but is illustrated as being a lever-actuated plunger device, which will retract a plug between the inner and outer layers 40,50 (in the separating membrane 72) to release the reagents into contact with each other. A close-up external perspective view of the lever mechanism is shown, illustratively, in FIG. 14A.

Alternative trigger mechanisms may be deployed in any of the foregoing embodiments, and any embodiment may employ two or more trigger mechanisms, rather than only one. For example, the membrane 72 between the inner reactor layer 40 and the outer reactor layer 50 may be made from a shape memory material, such as the nickel-titanium alloy "Nitinol", which can be deflected between two different positional arrangements, defined by two separate, stable crystal or molecular states or orientations within the material. The material may be selected to have a first known position, in which it forms a membrane separating the two layers 40,50, and a second position in which the material is retracted, due to folding or curling-up of the material when prompted to transition into the second position associated with a different crystal or molecular state or orientation. The transition between the "memorised" first and second states may be triggered by a force above a threshold magnitude applied during an impact ("passive"), or by application of heat or an electric current ("active", although motion can be used to generate electromagnetic signals or impulses, so it will not always be necessary to have an associated power supply). Membranes which will retract or otherwise release the reagents into contact in response to an applied voltage or current may be termed "electroreactive".

Similar structural arrangements can be configured using less specialised materials (an example from everyday life being the lids on metal tins, particularly if partially dented, which can be repetitively presses between slightly convex and slightly concave positions, but will remain in either position unless further restoring action is taken). Valve-based trigger arrangements will also be effective, depending on the particular reagents to be used and the particular intended application of the headwear.

It is also contemplated for the reagent in one of the layers 40, 50 (in the foregoing embodiments, the water in outer layer 50) to be contained in the layer under pressure, so as to cause the reagent to be forced into the adjacent layer, to mix with the other reagent, when the reaction is triggered.

Figure 15:
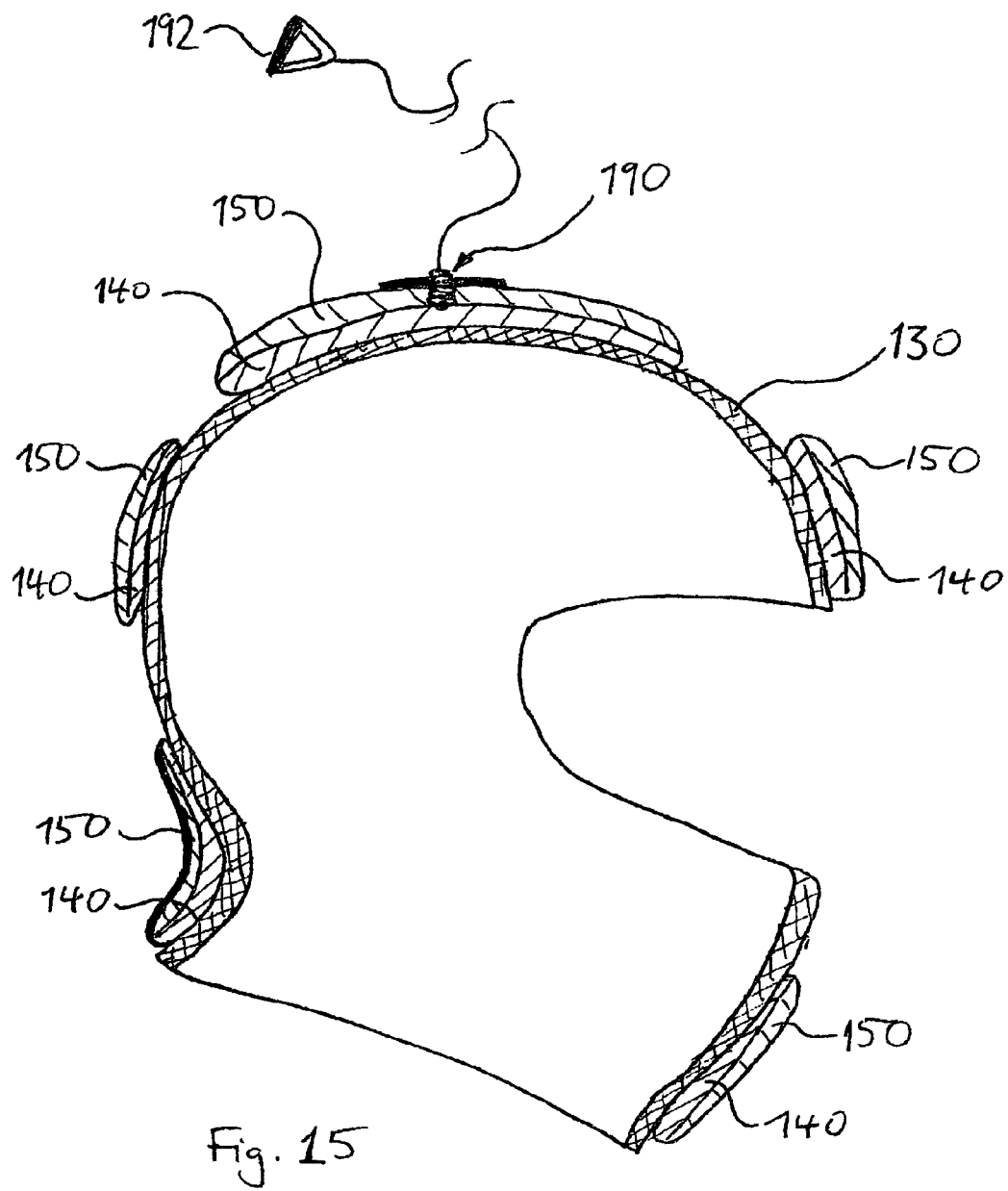
FIG. 15 is a cross-sectional side view of an embodiment of an item of headwear configured in accordance with the present invention, illustrating how the various fundamental principles of the present invention may be applied to a range of headwear items.

FIG. 15 shows how the basic principle of the present invention may be extended into alternative items of headwear, other than a motorcycle safety helmet. A head conforming member 130, which takes the form of a balaclava or similar item of headwear, is shown having a similar profile to the inner comfort layer 30 in the motorcycle safety helmet embodiments described above. It is contemplated that such an item of headwear could be worn in conjunction with another motorcycle safety helmet, if equipped with an appropriate trigger mechanism, rather than being integrated into the motorcycle safety helmet itself. This would allow existing motorcycle safety helmets to be upgraded in accordance with the present invention, relatively simply. Alternatively, the headwear is intended to be used as an item of emergency medical equipment for use by trained paramedics in the treatment of head injury victims, or may be utilised within a hospital environment to reduce brain swelling and neurological deterioration in trauma victims. Such a piece of equipment might have particular application to stroke victims, and might therefore be installed in first aid boxes, such as at sports venues and in offices and care homes.

The item of headwear may be configured as a balaclava, as illustrated in FIG. 15, or any other suitable shape for allowing easy application over and onto the head of a patient or other wearer of the headwear. One or a plurality of endothermic reactors are configured by respective inner layers 140 and 150, containing reagents which, when mixed or otherwise brought together, perform an endothermic reaction. The reactor layers are judiciously placed around the conforming member 130 to facilitate the ease with which the headwear can be placed onto a patient's head, and may be varied in size to adjust the extent and degree of cooling provided in each region of the head.

A trigger 190 similar to the emergency initiation device 90 of FIG. 14, is provided in order to initiate the reaction between the components in the inner and outer layers 140, 150 of the endothermic reactor. Pulling on the handle 192 removes the plunger 190 to remove the plug from the membrane separating the inner and outer layers 40,50.

It is, of course, possible in any embodiment, including the foregoing example embodiments, for the reagents to be provided other than in two layers. Reagents can be coupled that will sit side-by-side (for example, as crystals, or in a suspension), without reacting, until an initiation event takes place, such as passing a current through the adjacent or mixed reagents, or application of significant pressure, whereafter the reaction will proceed in a self-propagating fashion. Alternatively, the reagents may be formed into multiple alternating layers, or in a series of adjacent cells or pockets.

Whilst the invention has been described above with reference to specific exemplary embodiments, it is contemplated that practical applications will emerge in a number of areas. For example, helmets are worn in the majority of high-speed non-contact sports, such as motorcycle and motorcar racing, downhill skiing, etc. Similar safety helmets are also worn by the pilots of jet planes, as well as by police and military personnel. Helmets are also worn in certain contact sports, such as American football and ice hockey, although these sports necessarily involve significant amounts of contact, which could tend to induce triggering of the endothermic reactor in a non-critical event.

The invention claimed is:

1. Headwear comprising an endothermic reactor and a trigger to initiate an endothermic reaction in the endothermic reactor, the trigger initiating the endothermic reaction upon detection of an actual impact or an imminent impact to an outer surface of the headwear while being worn on a wearer's head, the trigger including means for detecting either deceleration of motion or acceleration of motion by the wearer of the headwear above either a threshold deceleration or above a threshold acceleration for initiating the endothermic reaction.

2. The headwear according to claim 1, wherein the headwear is a helmet for protection of a wearer's head from impacts.

3. The headwear according to claim 2, wherein the headwear is a motorcycle safety helmet.

4. The headwear according to claim 1, wherein the endothermic reactor comprises two or more reagents which will react together in an endothermic reaction, when the reaction is initiated.

5. The headwear according to claim 4, wherein each of the two or more reagents is contained in the endothermic reactor, separated from other reagents with which it will react, in respective cells or reservoirs.

6. The headwear according to claim 5, wherein at least one of the reagents is contained in a layer arranged to encompass substantially all or a part of the head of a wearer.

7. The headwear according to claim 5, wherein one or more membranes separate the reagents from each other, the trigger being configured to initiate the endothermic reaction by opening a hole in the membrane through which the separated reagents may be brought into contact.

8. The headwear according to claim 7, wherein the trigger includes a plunger for opening the hole in the membrane.

9. The headwear according to claim 7, wherein the trigger includes one or more frangible regions in the membrane, configured to open to form a hole when tension in the membrane exceeds a threshold magnitude.

10. The headwear according to claim 1, wherein the trigger comprises an element of electroreactive material for initiating the reaction in response to a signal generated by said detection.

11. The headwear according to claim 5, wherein the endothermic reactor is configured to contain the reagents and the reaction products of the endothermic reaction prior to and during the reaction.

12. The headwear according to claim 1, further including an emergency initiation device also operative to initiate the reaction.

13. A motorcycle safety helmet, comprising:
a rigid outer shell;
a layer of impact absorbing material inside the rigid outer shell;
an endothermic reactor, substantially contained inside the rigid outer shell, containing two or more reagents which will react together in an endothermic reaction to absorb heat from inside the helmet; and,
a trigger for initiating the endothermic reaction in the endothermic reactor, while being worn on a wearer's head, upon detection of an actual impact or an imminent impact to an outer surface of the helmet, the trigger including means for detecting either deceleration of motion or acceleration of motion by the wearer of the headwear above either a threshold deceleration or above a threshold acceleration for initiating the endothermic reaction.

14. The motorcycle safety helmet according to claim 13, wherein each of the two or more reagents is contained in the endothermic reactor, separated from other reagents with which it will react, in respective cells or reservoirs.

15. The motorcycle safety helmet according to claim 14, wherein at least one of the reagents is contained in a layer arranged to encompass substantially all or a part of the head of a wearer.

16. The motorcycle safety helmet according to claim 14, wherein one or more membranes separate the reagents from each other, the trigger being configured to initiate the endothermic reaction by opening a hole in the membrane through which the separated reagents may be brought into contact.

* * * * *